United States Patent [19]

Scott et al.

[11] Patent Number: 4,495,384

[45] Date of Patent: Jan. 22, 1985

[54] REAL TIME COCHLEAR IMPLANT PROCESSOR

[75] Inventors: Brian L. Scott, Denton; Wayne E. Kirkwood, Dallas, both of Tex.

[73] Assignee: Scott Instruments Corporation, Denton, Tex.

[21] Appl. No.: 410,628

[22] Filed: Aug. 23, 1982

[51] Int. Cl.³ .................................... H04R 25/00
[52] U.S. Cl. ............................. 179/107 FD; 128/784; 381/68
[58] Field of Search ........ 179/107 FD, 107 G, 107 R; 128/784, 419 R; 381/68

[56] References Cited

U.S. PATENT DOCUMENTS

| | | | |
|---|---|---|---|
| 3,116,458 | 12/1963 | Margopoulos | 328/135 |
| 3,221,253 | 11/1965 | Keyes | 324/103 P |
| 3,596,179 | 7/1971 | Hunter | 324/103 P |
| 3,753,109 | 8/1973 | Schainbaum | 324/103 P |
| 3,822,399 | 7/1974 | Grund et al. | 324/103 P |
| 3,896,375 | 7/1975 | Trolliet | 324/103 P |
| 3,903,470 | 12/1975 | Mirabile et al. | 324/77 A |
| 3,973,197 | 8/1976 | Meyer | 324/103 P |
| 3,999,125 | 12/1976 | Takeda et al. | 324/103 P |
| 4,038,568 | 7/1977 | May et al. | 307/351 |
| 4,063,048 | 12/1977 | Kissian, Jr. | 179/107 R |
| 4,284,856 | 8/1981 | Hochmair | 179/107 E |
| 4,357,497 | 11/1982 | Hochmair | 179/107 E |
| 4,400,590 | 8/1983 | Michelson | 128/784 |

FOREIGN PATENT DOCUMENTS 2811120 9/1978 Fed. Rep. of Germany ... 128/419 R

OTHER PUBLICATIONS

Atlas, Les E., Herndon, Matt K., Simmons, F. Blair, Dent, Laurel & White, Robert L., "Results of Stimulus and Speech Coding Schemes Applied to Multi-Channel Electrodes", Journal of the Acoustical Society of America.

Snow, Jr., James B., "Controversy in Otolaryngology", W. B. Saunders Company, 1980.
House, William F., Berliner, Karen I., Eisenberg, Laurie S., Edgerton, Bradly J., Thielemeir, Margaret A., "The Cochlear Implant: 1980 Update", Paper Presented at Collegium Oto-Rhino-Laryngologicum Amicitae Sacrum, San Francisco, CA, Sep. 1980.
White, Mark, "Design Considerations of a Prosthesis for the Profoundly Deaf", Copyright 1978.
White, R., "Review of Current Status . . . ", *IEEE Transactions on Biomedical Engineering*, vol. BME 29, No. 4, Apr. 1982.
Douek, E. et al., "A New Approach . . . ", *Otology*, vol. 70, Jun. 1977, pp. 379-383.

Primary Examiner—Gene Z. Rubinson
Assistant Examiner—L. C. Schroeder
Attorney, Agent, or Firm—Harold E. Meier

[57] ABSTRACT

A real time cochlear implant processor (10) receives an audio input signal and extracts spectrum segments by operation of bandpass filters (18, 20). In each channel temporal circuitry detects the zero slope points of the filtered audio input signal and generates a control signal which operates a gate (66). Amplitude circuitry includes a reference voltage source for providing positive and negative polarity signals for a first mode of operation. The reference signals are routed through the gate (66) by the control signals. In a second mode of operation the audio input signal, after logarithmic amplification, is passed through the gate (66) by operation of the control signals. In a third mode of operation the audio input signal is squared through infinite clipping and the resulting signal is gated by the control signals through the gate (66). The outputs of the channels are combined in a summing circuit (78) and passed through a buffer (82) to produce a driver signal for an auditory implant electrode. The pulse outputs from the plurality of channels have different amplitudes where the higher frequency channels have lower amplitude pulses.

34 Claims, 9 Drawing Figures

REAL TIME COCHLEAR IMPLANT PROCESSOR

TECHNICAL FIELD

The present invention pertains in general to an aid for hearing and in particular to an electronic circuit for generating speech content signals for driving an auditory implant electrode.

BACKGROUND OF THE INVENTION

Conventional hearing aids providing sound amplification do not provide any assistance to those persons classified as profoundly deaf. These persons have no measureable response to standardized hearing tests. Experimental tests have been conducted for profoundly deaf persons to implant an electrode into the cochlear region of the ear in the hope of electrically stimulating the nerves which transmits detected sounds to the brain.

It has been discovered that a conventional electrical audio signal, such as derived from a microphone, when applied to the implanted electrode, does not provide the stimulation for the subject corresponding to the sounds which generated the audio signal. It is therefore presumed that the ear must generate a neurological response which transmits the content of speech through the nerves of the ear to the brain in a manner distinctly different from the pure electrical analog of sound as transmitted through the air.

A number of experimentors have studied coding patterns for transforming an electrical audio signal into a driver signal for an auditory implant. To date, these tests have had only minimal success. Although subjects have been able to perceive the existence of the simulated sounds, the actual recognition and discrimination of words has been poor.

In view of the possibility of providing some degree of hearing ability to the profoundly deaf by means of auditory implants, there exists a need for a method and apparatus for encoding and processing speech signals in real time to provide a driver signal for an implant such that the subject is able to perceive and distinguish speech.

SUMMARY OF THE INVENTION

A selected embodiment of the present invention comprises an apparatus for generating a driver signal for an auditory implant electrode. The apparatus includes circuitry for receiving an audio input signal, together with means for detecting zero slope points of the audio input signal. Further circuitry is provided for generating the driver signal which has a pulse following the detection of each of the zero slope points of the audio input signal. Such a signal transmits the content of speech in such a manner that stimulates nerves to produce perceived sounds of speech to the subject.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION

The present invention is an apparatus for generating an electrical signal to drive an implanted electrode to produce sound sensations for persons who are profoundly deaf. It is well known that individual auditory neurons will phase lock to a stimulus waveform at frequencies of less than 4000 Hz. It has been shown that in the normal healthy mammalian system, different neurons will phase lock to different spectral regions of a complex waveform. This is largely due to the mechanics of the normal cochlea.

Patients currently selected for cochlear implants suffer from dysfunctional cochleas, but have some healthy active auditory neurons (typically 10% or less of the normal number of auditory neurons). The present invention discloses a means for causing different bundles of neurons to phase lock to different spectral regions of the stimulus waveform in the absence of a functional cochlea.

The basic concept is to utilize the patient's remaining amplitude detecting capabilities to force phase locking with different spectral regions. It is known that a given neuron has a limited dynamic range and that different neurons will respond to different amplitude regions. By presenting a pulsatile high frequency signal at one amplitude and a pulsatile low frequency signal at a different amplitude, phase-locking is induced to two different spectral regions. This phase-locking results in multiple frequencies being perceived through a single electrode implant. In other words, we are using amplitude coding to substitute for the normal spatial coding of frequency in the healthy cochlea.

The present invention is primarily designed for a single electrode implant, however, it can be usefully applied with a multi-electrode implant.

Figure 1:
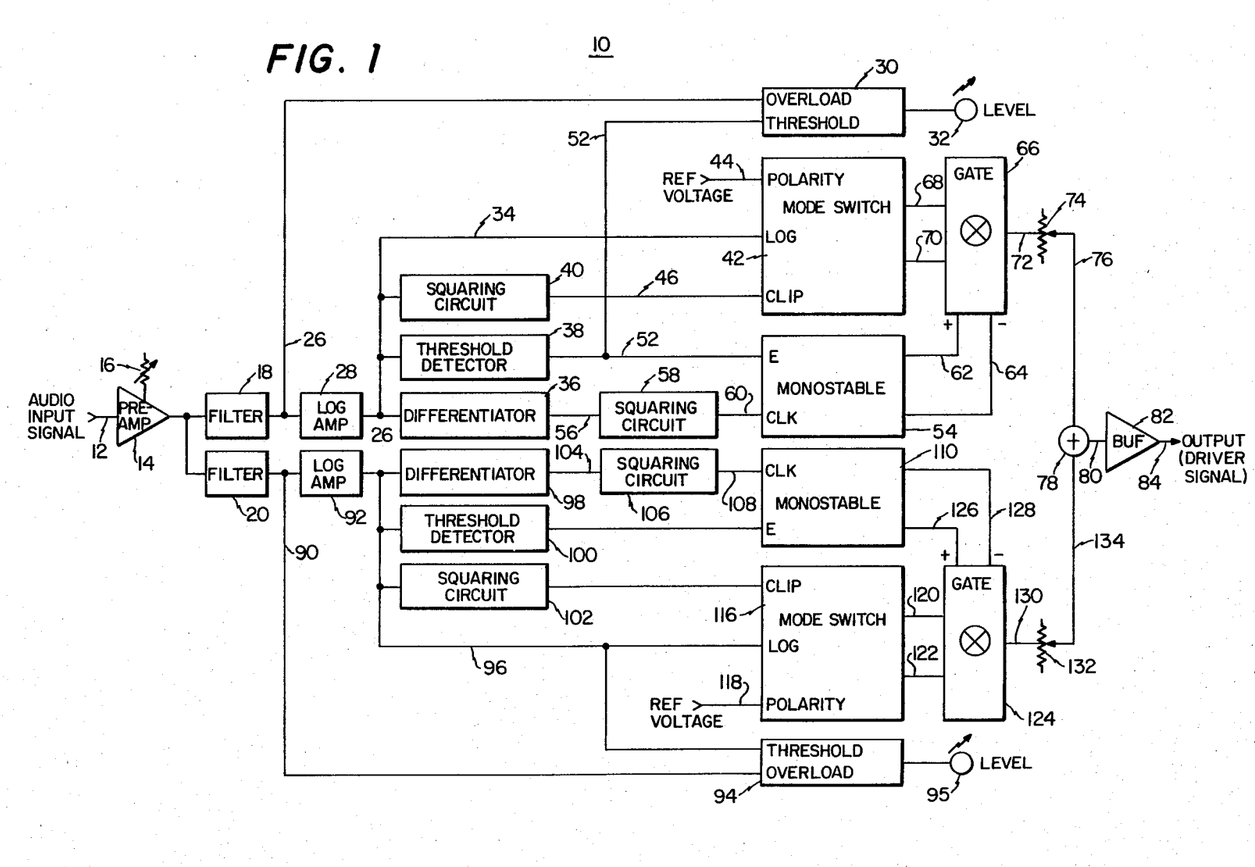
FIG. 1 is a block diagram of a two channel cochlear implant speech processor.

Referring now to FIG. 1 there is illustrated a block diagram of a preferred embodiment of the present invention. The overall circuit, termed a cochlear implant processor, is designated by the reference numeral 10. An audio input signal is transmitted through a line 12 to an amplifier 14. A potentiometer 16 serves as a level control for the amplifier 14. The output from the amplifier 14 is provided to the inputs of filters 18 and 20. These are preferably bandpass filters with filter 18 having a bandwidth of 0.3 to 1 kilohertz and filter 20 having a bandwidth from 1 to 5 kilohertz and both filters having a 24 db per octave rolloff.

The output from filter 18 is transmitted through a line 26 to a logarithmic amplifier 28. The output of filter 18 is further transmitted through line 26 to an overload and threshold circuit 30. Circuit 30 drives an LED 32.

The output from amplifier 28 is transmitted through a line 34 to a differentiator circuit 36, to a threshold detector circuit 38 and to a squaring circuit 40. The output of amplifier 28 is further transmitted through line 34 to the log input of a mode selection switch 42. There is provided a reference voltage input through a line 44 to the polarity input of switch 42. The output of the squaring circuit 40 is transmitted through a line 46 to the clip input of switch 42.

The output from the threshold detector circuit 38 is transmitted through a line 52 to the threshold input terminal of the overload and threshold circuit 30. The output from threshold detector circuit 38 is further provided to the enable input of a monostable circuit 54.

The output of the differentiator circuit 36 is transmitted through a line 56 to a squaring circuit 58. The output of the squaring circuit 58 is transmitted through a line 60 to the clock input of the monostable circuit 54. The monostable circuit 54 produces positive and negative control signals which are transmitted through lines 62 and 64 to the control input of a gate circuit 66. One of the three input signals selected by the mode switch 42 is transmitted through lines 68 and 70 to the input of the gate circuit 66. The output from the gate circuit 66 is transmitted through a line 72 to a level control potentiometer 74. From the potentiometer 74 the gated signal is transmitted through a line 76 to a summing circuit 78. The output of summing circuit 78 is transmitted through a line 80 to the input of a buffer 82. The output of the processor 10 is provided at a line 84 at the output of buffer 82.

The circuit 10 has two channels which correspond to the filters 18 and 20 and are respectively designated F1 and F2. The channel for filter 18 has been described above. The circuitry for the second channel corresponding to filter 20 is now described and is essentially the same as that described above.

The output of filter 20 is transmitted through a line 90 to a logarithmic amplifier 92 and to an overload and threshold circuit 94. Circuit 94 drives an LED 95.

The output of the logarithmic amplifier 92 is transmitted through a line 96 to a differentiator circuit 98, a threshold detector circuit 100, a squaring circuit 102, the log input of switch 116 and to the threshold input of the overload and threshold circuit 94.

The output from the differentiator circuit 98 is passed through a line 104 to a squaring circuit 106. The square wave output of the circuit 106 is transmitted through a line 108 to the clock input of a monostable circuit 110.

The output of the squaring circuit 102 is provided to the clip input of a mode selection switch 116. A reference voltage is provided through a line 118 to the polarity input of switch 116. The input selected by switch 116 is transmitted through lines 120 and 122 to a gate circuit 124. The output of the monostable circuit 110 is transmitted through line 126 and 128 to the control input of gate circuit 124.

The output of the gate circuit 124 is transmitted through a line 130 to a level control potentiometer 132.

From potentiometer 132 the output from the gate circuit 124 is transmitted through a line 134 to a second input of the summing circuit 78.

Figure 2:
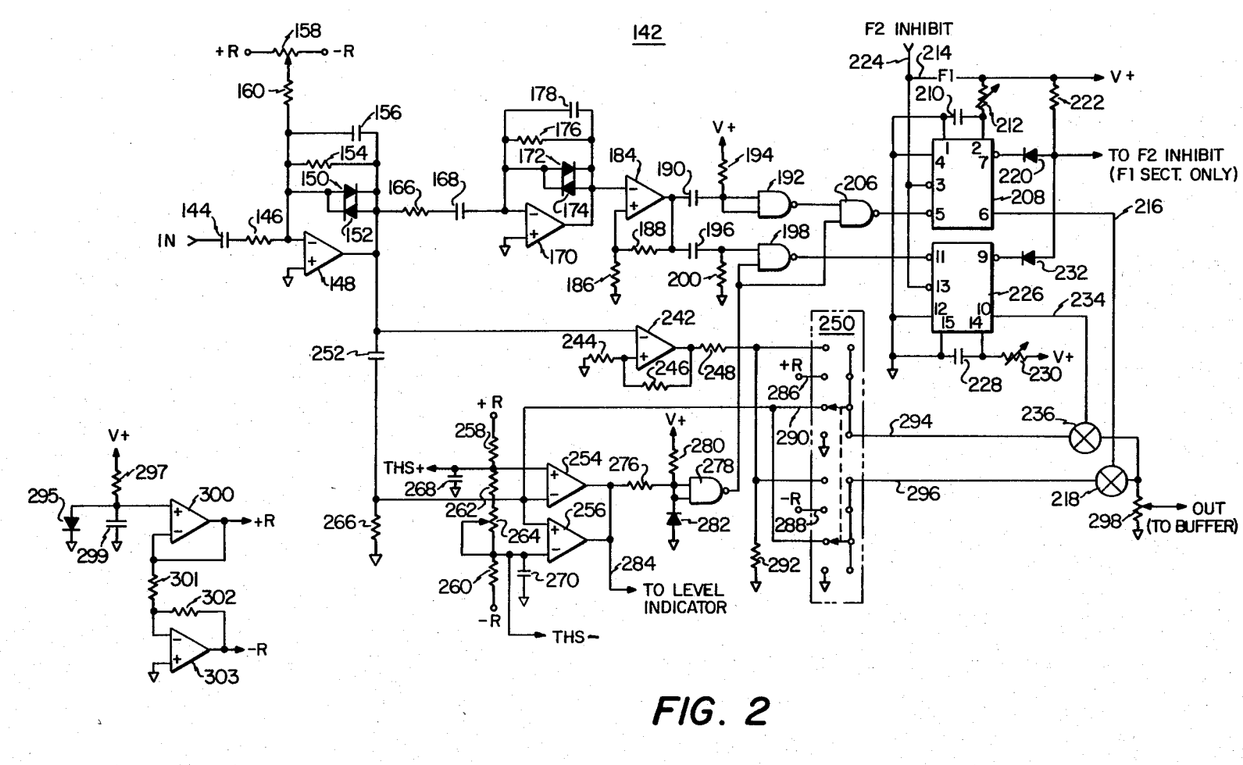
FIG. 2 is a detailed schematic diagram for one of the channels of the speech processor shown in FIG. 1.

Referring now to FIG. 2 there is illustrated a detailed schematic illustration of one of the two channels shown for the circuit 10 in FIG. 1. This figure shows the F1 channel and is designated by the reference numeral 142. Modifications are shown to illustrate the F2 channel. The F1 channel receives the output of the filter 18 which is passed serially through a capacitor 144 and a resistor 146. These components operate in conjunction with an operational amplifier 148 to function as a bipolar logrithmic amplifier. Oppositely biased diodes 150 and 152 are connected between the output and inverting input of amplifier 148. Also connected in parallel between the output and inverting input are a resistor 154 and a capacitor 156. The noninverting input of amplifier 148 is connected to ground. The diodes in the feedback network provide the logarithmic conversion and the resistor/capacitor combination limits the frequency response of the amplifier. An offset network includes a potentiometer 158 which is connected between reference voltages $+R$ and $-R$. A resistor 160 is connected between the inverting input of amplifier 148 and the wiper terminal of potentiometer 158. This combination of potentiometer and resistor serves to set the offset of the signal which passes through amplifier 148.

The output from the amplifier 148 is transmitted to a differentiator circuit which includes a resistor 166 and a capacitor 168. These components are connected serially between the output of amplifier 148 and the inverting input of an operational amplifier 170. The noninverting input of amplifier 170 is connected to ground. A pair of oppositely biased diodes 172 and 174 are connected between the output and inverting input of amplifier 170. Further connected between the output and inverting input of amplifier 170 are a resistor 176 and a capacitor 178. The diodes 172 and 174 serve to limit the peak-to-peak voltage of amplifier 170 and the resistor and capacitor 176 and 178 limit the frequency response of the amplifier.

The output of amplifier 170 is provided to the inverting input of an operational amplifier 184 which functions as a zero crossing detector. A resistor 186 is connected between the noninverting input of amplifier 184 and ground. A feedback resistor 188 is connected between the output and noninverting input of amplifier 184.

The output of amplifier 184 is provided to an edge detecting circuit. Specifically, the output of the amplifier is transmitted through a capacitor 190 to the inputs of a NAND gate 192 which functions as an inverter. A resistor 194 is connected between the input of NAND gate 194 and the voltage supply terminal $V+$. The output of amplifier 184 is further connected through a capacitor 196 to a first input of a NAND gate 198. A resistor 200 is connected between this first input and ground.

The output of NAND gate 192 is connected to a first input of a NAND gate 206.

The output of gate 206 is provided to pin 5 of a monostable circuit 208 which is a model CD4538. The width of the pulse produced by monostable circuit 208 is determined by a capacitor 210 connected between pins 1 and 2 and a potentiometer 212 which is connected between pin 2 and the positive supply $V+$. For the F1 channel there is provided a jumper 214 which is connected between the $V+$ supply and pin 3. The first output of the monostable circuit 208 is a control signal generated at pin 6 and this output is transmitted through a line 216 to a gate circuit 218. A control signal generated by the monostable circuit 208 and passed through the line 216 controls the gate 218. A second output at pin 7 of monostable circuit 208 is connected to the cathode of a diode 220 which has its anode connected to the first terminal of a resistor 222. The second terminal of resistor 222 is connected to the power terminal V+. For the F1 channel of the circuit 10 the junction of diode 220 and resistor 222 is connected to an F2 channel inhibit terminal. This inhibit terminal comprises a line 224 which is connected to pin 3 of monostable circuit 208. Such an inhibit line is provided only for the F2 channel.

The output of NAND gate 198 is transmitted to pin 11 of a monostable circuit 226 which is a part of the CD4538. The inhibit line 224 is connected to pin 13 of this monostable circuit in channel F2. The pulse width produced by monostable circuit 226 is determined by a capacitor 228 which is connected between terminals 14 and 15 and a potentiometer 230 which is connected between pin 10 and the positive supply V+. Pin 12 of monostable circuit 226 is connected to pin 4 of monostable circuit 208 and these pins are further connected to ground. The pin 9 output of monostable circuit 226 is connected to the cathode terminal of a diode 232 which has its anode terminal connected to the anode of diode 220. This connection provides the inhibit from monostable circuit 226 to the F2 channel. Another output of monostable circuit 226 is taken at pin 10 and is transmitted through a line 234 to a gate circuit 236. The monostable circuit 226 generates a control signal which is transmitted through line 234 to operate the gate circuit 236. The gate circuits 208 and 236 preferably comprise CMOS FETS such as a Model DG308C.

The output of the amplifier 148 is further provided to the inverting input of an operational amplifier 242 which functions as a squaring circuit to detect the zero crossover of the logarithmically amplified audio input signal. A resistor 244 is connected between the noninverting input of operational amplifier 242 and ground. A feedback resistor 246 is connected between the output and noninverting input of amplifier 242. The output from amplifier 242 is transmitted through a resistor 248 to a first input of a selector switch 250 and to a second input in the lower section of switch 250. A ground input is provided in both sections of switch 250 for an off state.

The output of the amplifier 148 is further transmitted through a capacitor 252 to a threshold circuit. Following the capacitor 252 the analog input signal is provided to the inverting input of an operational amplifier 254 and the noninverting input of an operational amplifier 256. A resistor 258 is connected between the +R reference and the noninverting input of amplifier 254. A resistor 260 is connected between the −R reference and the inverting input of amplifier 256. A resistor 262 and potentiometer 264 are connected serially between the noninverting input of amplifier 254 and the inverting input of amplifier 256. The wiper terminal of potentiometer 264 is further connected to the inverting input of amplifier 256. The adjustment of potentiometer 264 determines the detected threshold level for the signal provided to the threshold circuit. A resistor 266 is connected between the inverting input of amplifier 254 and ground.

A capacitor 268 is connected between the noninverting input of amplifier 254 and ground. A similar capacitor 270 is connected between the inverting input of amplifier 256 and ground. The adjusted threshold level taken at the junction of resistors 258 and 262 is connected to the THS+ input of channel F2. This input corresponds to the same point in channel F1. The junction of potentiometer 264 and resistor 260 is likewise connected with the THS− threshold input of channel F2.

The outputs of amplifiers 254 and 256 are tied together and are transmitted through a resistor 276 to the common inputs of a NAND gate 278. A resistor 280 is connected between the input of NAND gate 278 and the positive voltage supply V+. A diode 282 has the cathode terminal thereof connected to the inputs of NAND gate 278 and the anode terminal thereof connected to ground. The NAND gate 278 functions as an inverter. The output of NAND gate 278 is connected to the second input of NAND gate 198 and the second input of NAND gate 206 and serves as an enable control for the monostable circuits 208 and 226. The outputs of the amplifiers 254 and 256 are further transmitted through a line 284 to a level indicating circuit.

A second input to the switch 250 is the +R reference at a line 286. The −R reference is provided to an input at a line 288.

After the output of amplifier 148 is passed through capacitor 252 it is provided to input terminal 290 of the switch 250.

The switch 250 has two outputs designated as lines 294 and 296. Line 294 is connected to the input of gate circuit 236 and line 296 is connected to the input of gate circuit 218.

The outputs of gate circuits 236 and 218 are tied together and input to a potentiometer 298. The output of the channel is taken at the wiper terminal of the potentiometer 298 while the remaining terminal is connected to ground.

The reference signals +R and −R are generated in reference to a forward biased diode 295 which has its cathode grounded and its anode connected to the noninverting input of an operational amplifier 300. A resistor 297 is connected between the V+ terminal and the noninverting input of amplifier 300. A capacitor 299 is connected between ground and the noninverting input of amplifier 300. The output and inverting input of amplifier 300 are tied together. The +R reference is taken at the output of amplifier 300.

A resistor 301 is connected between the inverting input of amplifier 300 and the inverting input of an operational amplifier 303 which has its noninverting input grounded. A resistor 302 is connected between the output and inverting input of amplifier 303. The −R reference voltage is produced at the output of amplifier 303.

Figure 3:
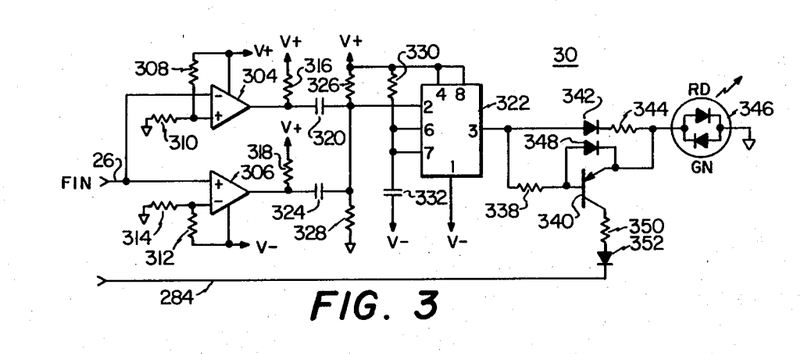
FIG. 3 is a detailed schematic diagram of the level and overload indicator circuit shown in FIG. 1.

The overload and threshold circuit 30 is shown in detail in FIG. 3. The output signal from the filter 18 is transmitted through the line 26 to the circuit 30. This signal is provided to the inverting input of an operational amplifier 304 and the noninverting input of an amplifier 306. Resistors 308 and 310 are connected serially between the V+ supply and ground with the junction of the resistors connected to the noninverting input of amplifier 304. Likewise, resistors 312 and 314 are connected serially between the V− supply and ground. The junction of these two resistors is connected to the inverting input of amplifier 306. A resistor 316 is connected between the V+ supply and the output of amplifier 304. A resistor 318 is connected between the V+ supply and the output of amplifier 306.

A capacitor 320 is connected between the output of amplifier 304 and pin 2 of a model 556 timer 322. A capacitor 324 is connected between the output of amplifier 306 and pin 2 of timer 322. Resistors 326 and 328 are connected serially between the V+ supply and ground with the junction of these resistors connected to pin 2 of timer 322. A resistor 330 is connected between the V+ supply and pins 6 and 7 of timer 322. A capacitor 332 is connected between pins 6 and 7 and the negative supply V−. Pins 4 and 8 of timer 322 are further connected to the V+ terminal. Pin 1 is connected to the V− terminal. The output of timer 322 is taken at pin 3 and is transmitted through a resistor 338 to the base terminal of a transistor 340.

The output of timer 322 at pin 3 is further transmitted through the serial connections of a diode 342 and a resistor 344 to the input of a two element LED 346. A diode 348 is connected between the base and emitter terminals of transistor 340 with the emitter terminal of the transistor further connected to the input of the LED 346. A resistor 350 is connected in series with a diode 352 between the collector terminal of transistor 340 and the output of the threshold detector circuit taken at line 284. The LED 346 comprises a forward based red emitting element connected between the input and a ground terminal and a reverse biased green element connected between the input and the ground terminal.

Figure 4:
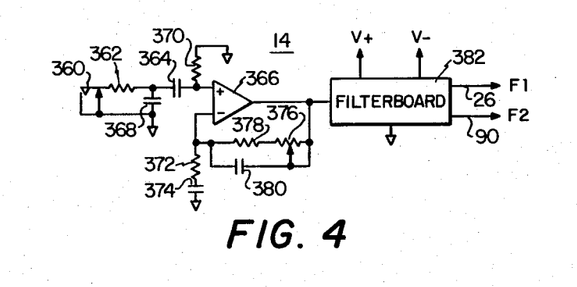
FIG. 4 is a detailed schematic diagram of the preamplifier for the speech processor shown in FIG. 1.

The amplifier circuit 14 is now described in reference to FIG. 4. The audio input signal is provided to an input socket 360 which has one terminal thereof connected to ground. The remaining terminal of socket 360 is connected to a resistor 362 which is in turn connected to a capacitor 364. The capacitor 364 is further connected to the noninverting input of an operational amplifier 366. A capacitor 368 is connected between the junction of resistor 362 with capacitor 364 and ground. A resistor 370 is connected between the noninverting input of amplifier 366 and ground. A series combination of a resistor 372 and a capacitor 374 is connected between the inverting input of amplifier 366 and ground. A series combination of a potentiometer 376 and a resistor 378 is connected between the output and inverting input of amplifier 366. The wiper terminal of potentiometer 376 is connected to the output of amplifier 366. A capacitor 380 is connected between the wiper terminal of potentiometer 376 and the inverting input of amplifier 366. The output of the operational amplifier 366 is input to a filter board 382 which has mounted thereon the filters 18 and 20. This filter board has connections to the V+ and V− power terminals as well as ground. The outputs of board 382 are the F1 channel and F2 channel signals at lines 26 and 90.

Figure 5:
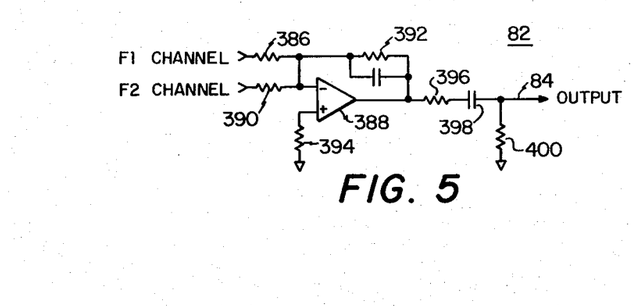
FIG. 5 is a detailed schematic diagram of the output buffer for the speech processor shown in FIG. 1.

The output buffer 82 shown in FIG. 1 is illustrated in a schematic diagram in FIG. 5. Inputs to the buffer 82 are provided at the wiper terminal of potentiometer 298 and the corresponding potentiometer for the F2 channel. The F1 channel input is transmitted through a resistor 386 to the inverting input of an operational amplifier 388. The F2 channel signal is transmitted through a resistor 390 also to the inverting input of operational amplifier 388. A feedback resistor 392 is connected between the output of amplifier 388 and its inverting input. A resistor 394 is connected between the noninverting input of amplifier 388 and ground. The output from amplifier 388 is transmitted serially through a resistor 396 and a capacitor 398 to the output line 84. A resistor 400 is connected between the output terminal 84 and ground.

The resistors 386 and 390 comprise a summing network for combining the outputs of the F1 and F2 channels to produce a single output driver signal. More resistors of this type can be added in parallel to handle any number of channels.

Figure 6:
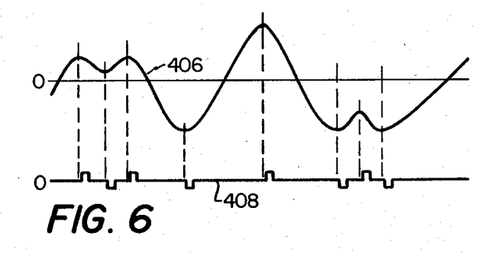
FIG. 6 is an illustration of an audio input signal together with the resulting pulse signal produced by one channel of the speech processor shown in FIG. 1 when the processor is operating in a reference polarity, mode.
Figure 7:
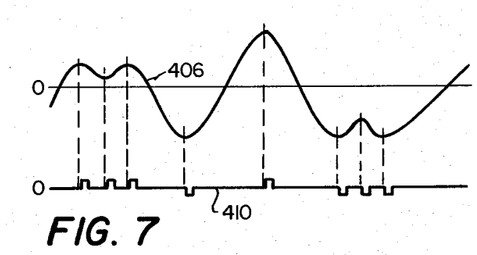
FIG. 7 is an illustration of waveforms produced for a channel in the speech processor of FIG. 1 showing the audio signal at the output of the filter and the resulting pulse signal produced by the channel when operating in an infinitely clipped mode.
Figure 8:
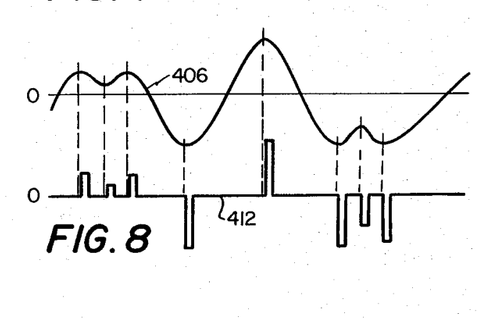
FIG. 8 is an illustration of the waveforms for a channel of the speech processor shown in FIG. 1 showing the output of a filter together with the pulse output of the channel when the channel is operating in a logarithmic mode wherein the pulses have amplitude modulation.

Referring now to FIGS. 6, 7 and 8 there are illustrated waveforms which represent signals in the circuits shown in FIGS. 1 and 2. A waveform 406 is presented as the upper trace in each of the FIGS. 6, 7 and 8. This waveform is measured at the output of either of the filters 18 or 20. In each of the FIGS. 6, 7 and 8 there is a lower waveform which is taken at the output of the gate circuit, such as 66 or 124, depending upon the setting of the mode selection switch 42 or 116. A lower waveform 408 in FIG. 6 represents the output of the gate circuit when the selector switch 42 is passing the polarity or reference signal from line 44 to the output. In FIG. 7 a waveform 410 represents the output of the gate circuit 66 when the selector switch 42 is set to the infinitely clipped position. In FIG. 8 a lower waveform 412 represents the output of the gate circuit 66 when the mode selector switch 42 is in the logarithmic position.

Figure 9:
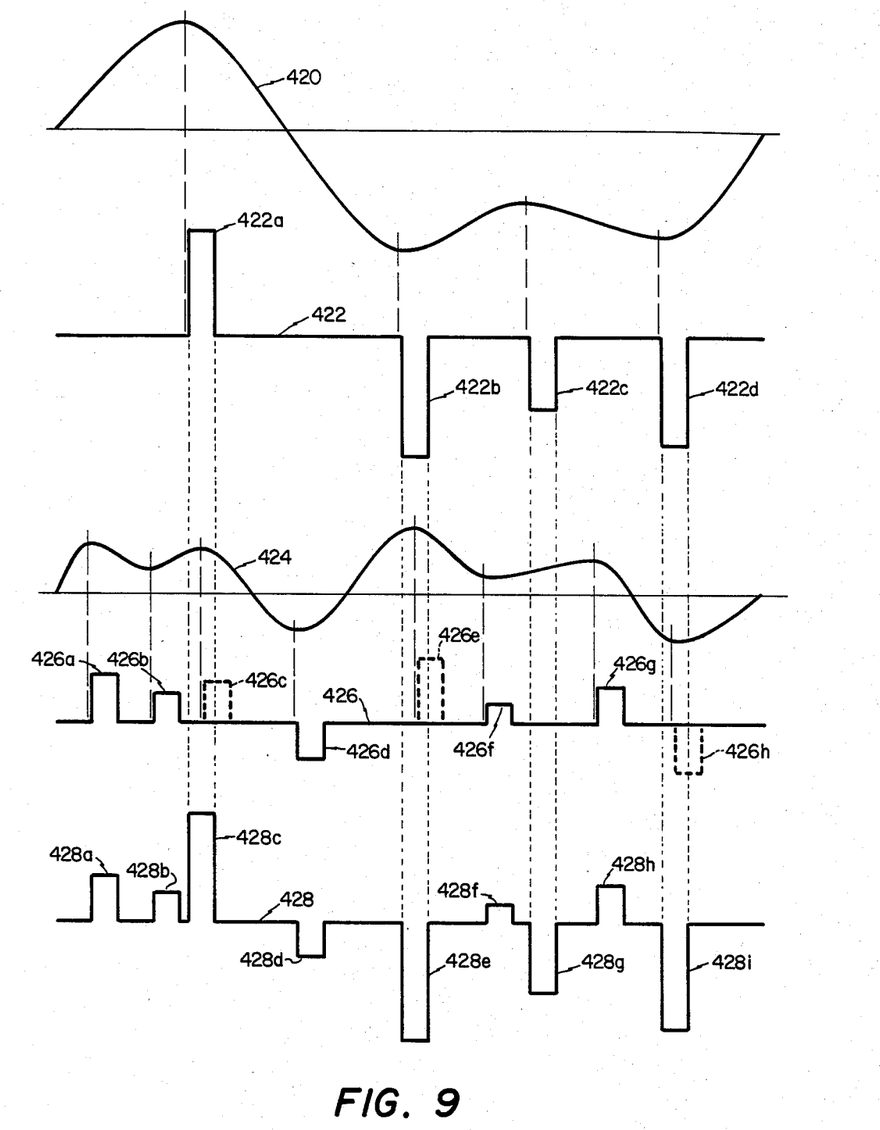
FIG. 9 is an illustration of waveforms showing low and high frequency channels and the corresponding pulse signals provided by each channel with the lower waveform being the summation of the two pulse signals wherein the low frequency pulses blank the time coincident high frequency pulses.

Referring to FIG. 9 there is illustrated waveforms which represent the concurrent operation of high and low frequency channels, such as channels F1 and F2, respectively. A waveform 420 represents a high amplitude, low frequency signal in channel F1. The amplitude modulated pulses produced by the F1 channel are shown as waveform 422. This is for operation in the logarithmic mode. These pulses are labeled with the reference numerals 422a through 422d. A small amplitude but relatively high frequency signal, corresponding to channel F2, is illustrated as waveform 424. The pulse signal produced for channel F2 is illustrated as waveform 426. These pulses are labeled 426a through 426h. Note that the amplitude of these pulses is substantially less than the amplitude of the pulses in the waveform 422. The combination of the two pulse waveforms 422 and 426 is illustrated as waveform 428. This is the output of the processor. Note that when there is a time coincidence of pulses for waveform 422, channel F1, these pulses serve to blank the production of corresponding time coincident pulses in channel F2. The blanked pulses in waveform 426 are illustrated as dashed lines since these pulses are in fact blanked, never generated, due to the existence of a corresponding pulse in the F1 channel.

Further referring to waveform 428 in FIG. 9 note that the high and low frequency pulses are separated by two distinct amplitude groupings. The low frequency pulses have high amplitude and the high frequency pulses have a lower amplitude. All of the low frequency pulses are included in the composite waveform while only the nonblanked high frequency pulses are included. As noted above, the remaining functional neurons have certain ones which respond to one amplitude region and other neurons which respond to different amplitude regions. By presenting a pulse type high frequency signal at one amplitude and a pulse type low frequency signal at another amplitude there can be phase-locking to two different spectral regions. This phase-locking results in multiple frequencies being perceived through a single electrode implant.

Operation of the real time implant processor of the present invention is now described in reference to the figures. The implant processor 10 shown in FIG. 1 includes monitor indicators and control functions so that the processor can be used for experimental purposes. However, the basic processor, without the test features, is designed for fabrication in a small package, such as integrated circuit form, for portable application by the user. The circuit is shown with two channels designated F1 and F2, however, the circuit can be usefully applied with one channel or with greater than two channels. In a system with a plurality of channels, each channel would process a selected spectrum segment, frequency band, of the audio signal provided to the processor.

The audio input signal, such as derived from a conventional microphone, is input through the amplifier 14 to boost the signal to a useful processing level. The audio signal is then passed through filters 18 and 20 to extract desired bands of frequency information. The filtered audio input signal at the output of filter 18 is monitored for threshold and over voltage by means of circuit 30. The filtered audio signal is also transmitted through the logarithmic amplifier 28 to compress the dynamic range of the audio signal.

Following the amplifier 28 the audio signal is input to a plurality of processing circuits. These circuits comprise a temporal group and an amplitude group. The temporal processing circuit determines the time sequence of the pulses comprising the implant driver signal at the output of the processor 10 while the amplitude circuits determine the polarity and amplitude of the pulses.

The temporal processing circuits include the differentiator 36, squaring circuit 58 and monostable circuit 54. The differentiator 36 differentiates the audio input signal to produce a differentiated audio input signal. The squaring circuit 58 greatly amplifies the differentiated audio input signal to produce a square wave signal having zero crossovers which correspond to the zero slope points of the input audio signal. The resulting square wave is input to the monostable circuit 54 wherein the transitions are utilized to trigger the monostable circuits. The pulses generated by the monostable circuit 54 comprise a control signal which is transmitted through lines 62 and 64 to operate the gate circuit 66.

The signal which is transmitted through the gate circuit 66 is selected by the switch 42. There are three active states as well as an off position. In a first position for switch 42 a reference voltage, having a positive polarity signal (+R) and a negative polarity signal (−R), is passed through the switch 42 to the gate circuit 66. These positive and negative signals are then combined for input to the summing circuit 78. The output is shown in FIG. 6 as waveform 408.

In the second mode, termed logarithmic, of the switch 42 the output of the logarithmic amplifier 28 is passed through the gate circuit 66. In this logarithmic mode pulses are generated by the operation of the gate circuit 66 with the pulses having the amplitude of the audio signal at the output of the amplifier 28 at the points of zero slope. This is illustrated as waveform 412 in FIG. 8.

In the third mode the switch 42 is set to receive the output of the squaring circuit 40. This circuit squares the audio signal at the output of the amplifier 28. This circuit produces zero crossovers at the zero crossover points of the audio signal. The circuit 40 produces a square wave signal in a manner which is termed "infinite clipping". This infinitely clipped signal is passed through the switch 42 to the gate 66. This signal results in the production of a pulse signal in which each of the pulses has the same polarity as the audio input signal at the zero slope points. The input signal and corresponding pulse signal waveform 410 for this mode are shown in FIG. 7. Note that when the audio input signal is in the positive region the pulses are positive and when the audio signal is in the negative region the pulses are negative. This is in contrast with the mode in FIG. 6 wherein the polarity of the pulses is dependent upon the slope of the audio signal immediately prior to the corresponding zero slope point.

As can be seen in FIGS. 6, 7 and 8 each channel of the processor 10, regardless of mode, produces a pulse immediately following the zero slope points of the audio input signal. In the polarity and infinitely clipped modes the pulses have fixed amplitudes but variable polarities. The amplitude of the pulses in waveforms 408 and 410 is approximately 0.8 volts peak-to-peak. In the logarithmic mode the pulses have different polarities but also have variable amplitude depending upon the amplitude of the audio signal. The amplitude of the pulses in waveform 412 is in the range of 0.8 to 1.6 volts peak-to-peak. This variable mode feature permits the testing of an individual subject to determine the best perception capability for the user. Once the optimum perception for an individual user has been determined, a portable device for a user need not have the selection capability.

In FIG. 8 the illustrated waveform 412 is shown inverted from that actually occurring in the circuit shown in FIG. 2. The pulses in FIGS. 6, 7 and 8 may also be delayed relative to the analog signal from which the pulse signals are produced.

The operation of one channel of the signal processor 10 is now described in reference to FIG. 2. The operational amplifier 148 together with the associated circuitry functions as the logarithmic amplifier 28 shown in FIG. 1. The operational amplifier 170 and its associated circuitry, including resistor 166 and capacitor 168, function as a differentiator circuit corresponding to the differentiator circuit 36 in FIG. 1. The squaring circuit 58 corresponds to the operational amplifier 184. The capacitors 190 and 196, together with the logic gates 192, 198 and 206 serve to detect the edges of the square wave signal produced by amplifier 184. These circuits produce triggering signals which are input to the monostable circuits 208 and 226. When the circuit 208 is triggered, a pulse is produced which is transmitted through line 216. Likewise, when circuit 226 is triggered, a pulse is produced which is transmitted through line 234. These pulses comprise control signals which operate the gate circuits 218 and 236. The width of the pulses produced by circuits 208 and 226 is determined by adjustment of the potentiometers 212 and 230 which are ganged together. If a fixed pulse width is desired, these potentiometers can be replaced by fixed impedance resistors.

The F1 channel is designed to inhibit the F2 channel such that pulses produced by the F1 channel blank those produced by the F2 channel. This inhibit function is produced by the signals at pins 7 and 9 of circuits 208 and 226. These signals are combined through diodes 220 and 232 and transmitted through the F2 inhibit line from the F1 channel to the F2 channel. In the F1 channel embodiment, the jumper 214 is provided and there is no inhibit signal input such as through line 224. In an embodiment having more than two channels, each subsequent channel can be blanked by the preceding channel.

In a further embodiment of the present invention each of the channels can be provided with a fixed pulse width without blanking between channels. In a selected embodiment the F1 channel has a pulse width of 30 microseconds and the F2 channel has a pulse width of 200 microseconds. With all channels the same, a pulse width of 60 microseconds is desired.

Further referring to FIG. 2, the operational amplifier 242 functions as a zero crossing detector and corresponds to the squaring circuit 40 in FIG. 1. The square wave signal produced by this circuit is input to the mode selection switch 250 which corresponds to the switch 42 in FIG. 1. The logarithmic input to switch 250 is provided from the output of amplifier 148 through capacitor 252. Reference voltage levels +R and −R are generated by a voltage reference circuit described above and input to the lines 286 and 288 of switch 250.

The threshold detector circuit, such as 38 in FIG. 1, corresponds to the operational amplifiers 254 and 256 together with the associated circuitry. The threshold level is set by operation of the potentiometer 264. This threshold level is transmitted to the other channels through the lines marked THS+ and THS−. When the output of the amplifier 148 does not exceed the set threshold, the amplifiers 254 or 256 produce a blanking signal which is passed through the gate 278 to inhibit the logic gates 192, 198 and 206 to therefore prevent the monostable circuits 208 and 226 from producing pulses. The threshold circuit serves to inhibit the production of a driver signal to the implant electrode to reduce the amount of noise which would otherwise be supplied to the user.

Referring now to FIG. 3 there is shown the overload and threshold circuit 30. This circuit receives the output of the filter 18 and serves to detect positive and negative overload conditions by operation of the operational amplifiers 304 and 306. The momentary overload conditions trigger the timer 322 which stretches the overload conditions to produce a driver signal for the LED 346. The stretched driver signals allow the LED to be activated for a sufficient time to be detected by an observer. The threshold signal, described above, is transmitted through line 284 to activate the LED 346 as well. The LED 346 has red and green elements. The red element is activated when the input signal is in an overload condition and the green element is activated when the input signal is above threshold but below overload.

Referring now to FIG. 4, there is shown the amplifier 14. The amplification is provided by the operational amplifier 366 together with its associated circuitry. This amplifier provides an approximately 50 db gain to permit the output signal of a microphone to be processed by the circuitry of the present invention. The filters 18 and 20 are included on the filter board 382. The design of these filters is conventional and is well known in the art.

The output buffer 82 is shown as a schematic diagram in FIG. 5. The F1 channel signal and the F2 channel signal are input to a resistor combining network comprising the resistors 386 and 390. The combined signal is then passed through the high impedance buffer comprising operational amplifier 388. The resulting signal is then passed to the output terminal 84 and comprises the driver signal for the audio implant electrode.

In summary, the present invention comprises a method and apparatus for producing a pulse type driver signal for an auditory implant electrode. Speech information is extracted from an audio signal by detecting the zero slope points of the signal and producing a corresponding pulse for each zero slope point. Various embodiments of the invention have fixed amplitude pulses, selective polarity pulses and pulses which have an envelope dependent upon the amplitude of the audio signal. Such driver signals, when supplied to the implant electrode, can provide the user with the sensation of sound in such a manner that words can be perceived and understood in many instances.

We claim:

1. Apparatus for generating a driver signal for an auditory implant electrode, comprising,
   means for receiving an audio input signal,
   means for detecting zero slope points of said audio input signal, and
   means for generating said driver signal having a pulse following the detection of each of said zero slope points of said audio input signal.

2. Apparatus as recited in claim 1 wherein said means for detecting comprises:
   a differentiation circuit connected to receive said audio input signal for producing a differentiated audio input signal,
   a squaring circuit connected to receive said differentiated audio input signal and producing a square wave signal therefrom, said square wave signal having zero crossovers corresponding to the zero slope points of said audio input signal, and
   means responsive to said square wave signal for generating triggering signals for driving said means for generating.

3. Apparatus for generating a driver signal for an auditory implant electrode, comprising:
   means for receiving an audio input signal,
   means for detecting zero slope points of said audio input signal, and
   means for generating said driver signal having first polarity pulses and second polarity pluses with fixed amplitudes, said means for generating producing the first polarity pulses when a zero slope point immediately follows a positive going portion of the audio input signal and the second polarity pulses when the zero slope point immediately follows a negative going portion of the audio input signal.

4. Apparatus for generating a driver signal for an auditory implant electrode, comprising:
   means for receiving an audio input signal,
   means for detecting zero slope points of said audio input signal, and
   means for generating said driver signal having pulses of a first polarity when the zero slope points are in the positive region of the audio input signal and of a second polarity when the zero slope points are in a negative region of the audio input signal.

5. Apparatus as recited in claim 4 wherein said means for generating produces said first polarity pulses and said second polarity pulses having fixed amplitudes.

6. Apparatus as recited in claim 4 wherein said pulses each have an amplitude porportional to the amplitude of said audio input signal at the corresponding zero slope point.

7. Apparatus for generating a driver signal for an auditory implant electrode, comprising:
   means for receiving an audio input signal,
   means for detecting zero slope points of said audio input signal and for generating a control signal having a temporary active state following the detection of each of said zero slope points, and gate means operated by said control signal for selectively passing a designated signal therethrough to produce said driver signal at the output of said gate means, said driver signal comprising a series of pulses each corresponding to one of said zero slope points of said audio input signal.

8. Apparatus as recited in claim 7 wherein said means for detecting comprises:
   a differentiation circuit connected to receive said audio input signal for producing a differentiated audio input signal,
   a squaring circuit connected to receive said differentiated audio input signal and producing a square wave signal having zero crossovers corresponding to the zero slope points of said audio input signal,
   means responsive to said square wave signal for generating triggering signals, and
   first and second monostable circuits generating pulse output signals comprising said control signal.

9. Apparatus as recited in claim 7 including means for generating fixed amplitude positive and negative polarity signals which comprise said designated signal.

10. Apparatus for generating a driver signal for an auditory implant electrode, comprising,
   means for receiving an audio input signal,
   a plurality of channels each comprising:
      a filter for passing said audio input signal therethrough,
      means for detecting zero slope points of said filtered audio input signal and for generating a control signal having a temporary active state following the detection of each of said zero slope points,
      gate means operated by said control signal for selectively passing a designated signal therethrough to produce an output signal, and means for combining the output signals from each of said channels to produce said driver signal.

11. Apparatus as recited in claim 10 wherein said means for detecting comprises:
   a differentiation circuit connected to receive said audio input signal for producing a differentiated audio input signal,
   a squaring circuit connected to receive said differentiated audio input signal and producing a square wave signal therefrom, said square wave signal having zero crossovers corresponding to the zero slope points of said audio input signal,
   means responsive to said square wave signal for generating triggering signals, and
   first and second monostable circuits responsive to said triggering signals for generating pulse output signals comprising said control signal.

12. Apparatus as recited in claim 10 including means for generating fixed amplitude positive and negative polarity signals which comprise said designated signal.

13. Apparatus as recited in claim 10 including means for infinitely clipping said audio input signal to produce said designated signal.

14. Apparatus as recited in claim 10 including means for logarithmically amplifying said audio input signal to produce said designated signal.

15. A method for generating a driver signal for an auditory implant electrode, comprising the steps of:
   receiving an audio input signal,
   detecting zero slope points of said audio input signal, and
   generating said driver signal by producing a pulse following the detection of the zero slope points of said audio input signal.

16. A method as recited in claim 15 wherein said step of detecting zero slope points comprises the steps of:
   differentiating said audio input signal to produce a differentiated audio input signal,
   squaring said differentiated audio input signal to produce a square wave signal wherein said square wave signal has zero crossovers corresponding to the zero slope points of said audio input signal, and
   means responsive to said square wave signal for generating triggering signals for said step of generating said driver signal.

17. Apparatus for generating a driver signal for an auditory implant electrode, comprising:
   means for receiving an audio input signal,
   means for detecting zero slope points of said audio input signal,
   first and second monostable circuits responsive to the output of said means for detecting for generating respective first and second pulse signals,
   gate means controlled respecitvely by said first and second pulse signals and having respective gate input signals, and
   means for combining the output of said gate means to produce the driver signal.

18. Apparatus for generating a driver signal for an auditory implant electrode, comprising:
   means for receiving an audio input signal,
   means for infinitely clipping the audio input signal to produce a designated signal,
   means for detecting zero slope points of said audio input signal and for generating a control signal having a temporary active state following the detection of each of said zero slope points, and
   gate means operated by said control signal for selectively passing the designated signal therethrough to produce said driver signal at the output of said gate means, said driver signal comprising a series of pulses each corresponding to one of the zero slope points of the audio input signal.

19. Apparatus for generating a driver signal for an auditory implant electrode, comprising:
   means for receiving an audio input signal,
   means for logarithmically amplifying the audio input signal to produce a designated signal,
   means for detecting zero slope points of said audio input signal and for generating a controlled signal having a temporary active state following the detection of each of the zero slope points, and
   gate means operated by the control signal for selectively passing the designated signal therethrough to produce said driver signal at the output of said gate means, said driver signal comprising a series of pulses each corresponding to one of the zero slope points of the audio input signal.

20. A method for generating a driver signal for an auditory implant electrode, comprising the steps of:
   detecting zero slope points of a received audio input signal,
   generating the driver signal that includes pulses having a first polarity when the detected zero slope point immediately follows a positive going portion of the audio input signal and pulses having a second polarity when the detected zero slope point immediately follows a negative point portion of the audio input signal.

21. A method as recited in claim 20 wherein said first polarity pulses and said second polarity pulses have fixed amplitudes.

22. A method for generating a driver signal for an auditory implant electrode, comprising the steps of:
   detected zero slope points of a received audio input signal, and
   generating the driver signal having pulses of a first polarity when the detected zero slope points are in the positive region of the audio input signal and pulses having a second polarity when the detected zero slope points are in the negative region of the audio input signal.

23. A method as recited in claim 22 wherein said first polarity pulses and said second polarity pulses have the same amplitude.

24. A method as recited in claim 22 wherein each of said pulses has an amplitude proportional to the amplitude of said audio input signal at the corresponding zero slope point.

25. A method for generating a driver signal for an auditory implant electrode, comprising the steps of:
   receiving an audio input signal,
   detecting zero slope points of said audio input signal and generating a control signal having a temporary active state following the detection of each of said zero slope points, and
   opening a gate in response to said control signal to pass a designated signal therethrough to produce said driver signal at the output of said gate, said driver signal comprising a series of pulses each corresponding to one of said zero slope points of said audio input signal.

26. A method for generating a driver signal for an auditory implant electrode, comprising the steps of:
   detecting zero slope points of a received audio input signal and generating a control signal having a temporary active state following the detection of each of the zero slope points,
   generating fixed amplitude positive and negative polarity signals comprising a designated signal, and
   in response to said control signal gating the designated signal to produce the driver signal, the driver signal comprising a series of pulses each corresponding to one of the zero slope points of the audio input signal.

27. A method as recited in claim 26 including a step of infinitely clipping said audio input signal to produce said designated signal.

28. A method as recited in claim 26 including a step of logarithmically amplifying said audio input signal to produce said designated signal.

29. A method for generating a driver signal for an auditory implant electrode, comprising the steps of:
   receiving an audio input signal,
   processing said audio input signal through a plurality of channels each corresponding to a spectrum segment of said audio input signal, the processing in each channel comprising the steps of:
      passing said audio input signal through a filter to extract a selected frequency band signal of said audio input signal,
      detecting the zero slope points of said selected frequency band signal,
      generating a control signal having a temporary active state immediately following the detection of each of said zero slope points of said selected frequency band signal,
      opening a gate in response to said control signal to pass a designated signal therethrough to produce an output signal having a pulse corresponding to each of the detected zero slope points of said selected frequency band signal, and
   combining the output signals from each of said channels to produce said driver signal.

30. A method as recited in claim 29 including a step of generating fixed amplitude positive and negative polarity signals which comprise said designated signal.

31. A method as recited in claim 29 including a step of infinitely clipping said selected frequency band signal to produce said designated signal.

32. A method as recited in claim 29 including a step of logarithmically amplifying said audio input signal to produce said designated signal.

33. Apparatus for generating a driver signal for an auditory implant electrode, comprising:
   means for receiving an audio stimulus waveform;
   means for causing neurons to phase lock to selected spectral regions of the stimulus waveform, said means including means for generating a pulsitale high frequency signal at one amplitude to be phase locked to one spectral region and means for generating a pulsitale low frequency signal at a second amplitude to be phase locked to a second spectral region.

34. Apparatus for generating a driver signal as set forth in claim 33 wherein said means for generating the driver signal includes means for generating frequency signals for each of the spectral regions.

* * * * *